United States Patent
Bombardelli et al.

(10) Patent No.: US 7,128,932 B2
(45) Date of Patent: Oct. 31, 2006

(54) FORMULATIONS USEFUL IN THE TREATMENT OF MALE AND FEMALE IMPOTENCE

(75) Inventors: Ezio Bombardelli, Milan (IT); Paolo Morazzoni, Milan (IT); Antonella Riva, Milan (IT); Roberto Seghizzi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/513,730

(22) PCT Filed: Apr. 30, 2003

(86) PCT No.: PCT/EP03/04528

§ 371 (c)(1),
(2), (4) Date: Nov. 8, 2004

(87) PCT Pub. No.: WO03/094943

PCT Pub. Date: Nov. 20, 2003

(65) Prior Publication Data

US 2005/0220905 A1    Oct. 6, 2005

(30) Foreign Application Priority Data

May 10, 2002  (IT)  .......................... MI2002A0990

(51) Int. Cl.
*A61K 36/16* (2006.01)
*A61K 36/54* (2006.01)

(52) U.S. Cl. ...................... 424/739; 424/752; 424/725; 562/560

(58) Field of Classification Search .................... None
See application file for complete search history.

(56) References Cited

U.S. PATENT DOCUMENTS

| 6,444,237 B1 * | 9/2002 | Heleen ....................... 424/725 |
| 6,803,060 B1 * | 10/2004 | Reyes ......................... 424/769 |
| 2003/0068391 A1 * | 4/2003 | Harris et al. ................ 424/750 |

OTHER PUBLICATIONS

A. Adimoelja: "Phytochemicals and the breakthrough of traditional herbs in the management of sexual dysfunctions" International Journal of Andrology, vol. 23, No. sup 2, 2000, pp. 82-84, XP001148732 p. 82.
Database WPI Week 200102 Derwent Publications Ltd., London, GB; AN 2001-014152 XP002251655 N.P. Nechaeva: "Homeopathic medicinal agent for treatment of impotency" & RU 2 153 347 C (N.Doktor), Jul. 27, 2000 abstract.
R.Stanislavov, V. Nikolova: "The effect of Tribulus terrestris on male fertility" American Journal of Reproductive Immunology, vol. 46, No. 1, 2001, p. 91 XP008014359 p. 91.

* cited by examiner

*Primary Examiner*—Susan D. Coe
(74) *Attorney, Agent, or Firm*—Young & Thompson

(57) ABSTRACT

Disclosed are pharmaceutical compositions containing: extracts of *Tribulus terrestris*, *Turnera diffusa* and *Cinnamon cassia* in the weight ratio of 1.5–3.5:1–2:0.1–0.4 respectively; *Ginkgo biloba* extract, and optionally arginine or a physiologically equivalent esters salts or precursor thereof. The compositions according to the invention are useful in the treatment of male and female sexual dysfunctions.

11 Claims, No Drawings

FORMULATIONS USEFUL IN THE TREATMENT OF MALE AND FEMALE IMPOTENCE

The present invention relates to formulations which are useful in the treatment of male and female sexual dysfunctions.

Sexual dysfunctions have considerable importance, and form the subject of intensive biomedical research efforts. According to recent statistics, the problem of impotence in its various forms (absence of libido and erectile dysfunctions) affects some 70% of the population aged approx. 50 and over. The degree of impotence in its various forms obviously varies in severity, especially among the elderly, where it is often physiologically associated with other disorders such as heart or kidney disease.

The drugs now available to treat such dysfunctions, especially erectile dysfunction, include hormones such as testosterone, VIP, prostaglandin derivatives ($PGE_s$), and cardiovascular agents such as papaverine, phenoxybenzamine and phentolamine.

However, none of these drugs provides a satisfactory, permanent solution to the problem, because of the side effects they cause and the need for an intercavernous or intraurethral injection in the case of papaverine and PGE2, for example.

Recently, cGMP phosphodiesterase inhibitors have been developed which are particularly useful in the treatment of impotence, and are active by the oral route. One of these agents, called Sildenafil (WO 94/28902), is already on the market.

Here again, however, the side effects are by no means negligible, and the need for safer and more effective treatments is still strongly felt.

Numerous products of natural origin (mainly plant- but also animal-based) are now being studied by modern pharmacology, on the basis of indications obtained from traditional medicine, to evaluate the possible scientific basis for their empirical use.

Biochemical studies have demonstrated the great complexity of the mechanisms involved in the physiological processes associated with sexual activity, such as penile and clitoral erection, vaginal lubrication, ejaculation and orgasm.

Mediators such as nitric oxide (NO), the enzyme factors involved in the metabolism of the cAMP and cGMP messengers, the adrenergic receptors of the smooth muscle cell membranes, dopaminergic neurotransmitters, and the receptors of $PGE_s$ or other hormones are the possible targets of a pharmacological treatment for impotence and other sexual dysfunctions.

It is obviously difficult to provide a satisfactory solution to this specific problem, partly because in addition to the purely biochemical and physiological aspects there are also environmental and psychological factors which can further complicate the clinical picture of patients suffering from sexual disorders.

It has now been found that a combination of extracts of medicinal plants with specific properties, in certain quantity ratios, gives particularly satisfactory therapeutic results in the treatment of male and female sexual dysfunctions.

The invention relates in particular to pharmaceutical compositions containing:

extracts of *Tribulus terrestris, Turnera diffusa* and *Cinnamon cassia* in the weight ratio of 1.5–3.5:1–2:0.1–0.4 respectively;

*Ginkgo biloba* extract, and possibly arginine or a physiologically equivalent ester, salt or precursor thereof in admixture with a suitable carrier or excipients.

Extracts of *Tribulus terrestris, Turnera diffusa* and *Cinnamon cassia* are known and already used in some types of traditional medicine for similar purposes but no combination thereof is known even less in the specific quantitative ratios stated above.

In particular, *Tribulus terrestris* extract is known to induce synthesis of testosterone, a hormone responsible for stimulating sexual desire in both men and women; the extract of *Turnera diffusa*, which is rich in essential oils, has a vasodilating effect mediated by NO release, so that the extract performs a vasokinetic activity on the arteries and arterioles; *Cinnamon cassia* extract indirectly stimulates the libido by acting on the pleasure-related dopamine receptors.

Finally, the strong anti-phosphodiesterase activity of the dimeric flavones extracted from *Ginkgo biloba* contributes to the vasodilatation of the *corpora cavernosa*, thus boosting the vascular effect of *Turnera diffusa*.

However, the therapeutic results obtainable with the compositions of the invention cannot be explained solely on the basis of the activity of each extract; in fact, it has surprisingly been found that when the extracts are associated in quantitative ratios different from those stated above, they remain inactive, and can even aggravate the disorder. A real increase in sexual activity can therefore only be obtained by using the extracts of the various plants in a precise ratio which increases both libido and the blood supply to the genital organs.

The weight ratio of extracts of *Tribulus terrestris, Turnera diffusa* and *Cinnamon cassia* is preferably 2.5:1.5:0.2.

Arginine, its salt, ester or precursor, when used, is present in a quantitative ratio of between 0.5 and 1.5, preferably 1, to the plant extracts.

*Ginkgo biloba* extract is preferably constituted by a fraction of apigenin dimeric flavonoids, preferably added to the composition according to the invention in doses which guarantee a daily intake of 50 mg of said fraction.

Extracts of the medicinal plants specified above, obtained by conventional techniques such as extraction with solvents or supercritical fluids, can be used for the purposes of this invention.

However, the use of standardised extracts with a predetermined content of certain characteristic components of the extract is preferred:

for example, *Tribulus terrestris* extract will contain approx. 40% of saponins expressed as dioscin; *Turnera diffusa* extract is preferably a lipophilic extract; *Ginkgo biloba* extract preferably has a dimeric flavone content of approx. 60%; and *Cinnamon cassia* extract preferably has a cinnamic aldehyde content of approx. 70%.

When preparing the extracts, various parts of the plants can be used, as they contain the active constituents in different concentrations. The whole plant is used to prepare *Turnera diffusa* extracts in particular, preferably extracted with carbon dioxide under supercritical conditions at pressures of between 230 and 250 bars, preferably 240 bars, and at a temperature of between 35 and 55° C., preferably 40° C.; *Tribulus terrestris* extracts are preferably obtained from the aerial parts and seeds of the plant by extraction with a 40% ethanol/water mixture, while *Cinnamon cassia* extracts are preferably prepared by extraction from the bark of the trunk with carbon dioxide under supercritical pressure conditions of between 110 and 150 bars, preferably 135 bars, at the temperature of 35° C. *Ginkgo biloba* extract is preferably prepared from a fraction consisting of dimeric flavones deriving from apigenin which are prepared, for example, according to EP 360556.

The invention also relates to the use of extracts of *Tribulus terrestris*, *Turnera diffusa* and *Cinnamon cassia* in the weight ratio of 1.5–3.5:1–2:0.1–0.4 respectively in association with *Ginkgo biloba* extract, and optionally arginine or a physiologically equivalent ester, salt or precursor thereof, to prepare medicines for the treatment of male and female sexual dysfunctions, and especially for the treatment of impotence, libido disorders, frigidity and anorgasmia.

The mixture of extracts to which the invention relates must be taken chronically, not just immediately before sexual intercourse, although in some individuals the response takes place on the first treatment, within 30 minutes of taking the drug.

As an alternative to the plant extracts, the corresponding isolated active ingredients may be used, particularly dioscin, dimeric flavone of *ginkgo biloba*, and cinnamic aldhyde in combination with a lipophilic extract of *Turnera diffusa*. The use of said combination for the preparation of a medicament for the treatment of impotence, erectile dysunction, libido disorders, frigidity and anorgasmia as well as the medicaments comprising said combination are further objects of the invention.

Chronic administration of the compositions of the invention does not cause any significant side effects, is well tolerated, and does not alter the delicate hormone balances, especially the androgen/oestrogen balance, which govern major physiological events in men and women such as the andropause and the menopause.

Examples of suitable forms of administration of the compositions of the invention include tablets, soft and hard gelatin capsules, suppositories and drinkable preparations containing unit doses of between 100 and 300 mg of *Tribulus terrestris* extract and unit doses of the other components in accordance with the weight ratios specified above. Solid-phase formulations such as unmodified-release or gastroresistant tablets or drinkable liquid forms are particularly preferred.

The following examples are given to illustrate the invention rather than to limit its scope.

EXAMPLE 1

Preparation of Coated Tablets

Each 700 mg coated tablet contains:

| | |
|---|---|
| *Tribulus terrestris* | 250.00 mg |
| *Turnera diffusa* | 150.00 mg |
| *Cinnamon cassia* | 20.00 mg |
| *Ginkgo biloba* | 50.00 mg |
| L-arginine | 100.00 mg |
| Soya polysaccharides | 55.00 mg |
| Silicon dioxide | 14.00 mg |
| Silicified microcrystalline cellulose | 42.00 mg |
| Magnesium stearate | 4.00 mg |
| Hydroxypropyl methylcellulose | 6.40 mg |
| Talc | 5.20 mg |
| Titanium dioxide | 2.00 mg |
| Glycerin | 0.12 mg |
| Polysorbate 80 | 0.80 mg |
| Quinoline | 0.43 mg |
| Indigotine | 0.05 mg |

EXAMPLE 2

Preparation of Hard Gelatin Capsules

Each 340 mg capsule contains:

| | |
|---|---|
| *Tribulus terrestris* | 125.00 mg |
| *Turnera diffusa* | 75.00 mg |
| *Cinnamon cassia* | 10.00 mg |
| *Ginkgo biloba* | 25.00 mg |
| L-arginine | 50.00 mg |
| Soya polysaccharides | 25.00 mg |
| Silicon dioxide | 7.00 mg |
| Silicified microcrystalline cellulose | 20.00 mg |
| Magnesium stearate | 1.50 mg |
| Talc | 1.50 mg |

EXAMPLE 3

Preparation of Soft Gelatin Capsules

Each 700 mg soft gelatin capsule contains:

| | |
|---|---|
| *Tribulus terrestris* | 125.00 mg |
| *Turnera diffusa* | 75.00 mg |
| *Cinnamon cassia* | 10.00 mg |
| *Ginkgo biloba* | 25.00 mg |
| L-arginine | 50.00 mg |
| Soya lecithin | 20.00 mg |
| Medium-chain triglycerides | 100.00 mg |
| Polysorbate 80 | 10.00 mg |
| Soya oil | 275.00 mg |
| Colloidal silicon dioxide | 10.00 mg |

EXAMPLE 4

Preparation of a Drinkable Solution

Each 10 mL vial contains:

| | |
|---|---|
| *Tribulus terrestris* | 250.00 mg |
| *Turnera diffusa* | 150.00 mg |
| *Cinnamon cassia* | 20.00 mg |
| *Ginkgo biloba* | 50.00 mg |
| L-arginine hydrochloride | 100.00 mg |
| Glycerin | 3000.00 mg |
| Polysorbate 20 | 800.00 mg |
| Propylene glycol | 1000.00 mg |
| Acesulfame K | 175.00 mg |
| Sodium saccharine | 40.00 mg |
| Neohesperidine DC | 2.50 mg |
| Flavouring | 300.00 mg |
| Potassium sorbate | 11.70 mg |
| Methyl paraben | 8.30 mg |
| Purified water | q.s. to 10.00 mL |

EXAMPLE 5

Preparation of a Soluble Granulate

Each 5000 mg sachet contains:

| | |
|---|---|
| *Tribulus terrestris* | 250.00 mg |
| *Turnera diffusa* | 150.00 mg |

-continued

| | |
|---|---|
| Cinnamon cassia | 20.00 mg |
| Ginkgo biloba | 50.00 mg |
| L-arginine hydrochloride | 100.00 mg |
| Polysorbate 20 | 500.00 mg |
| Acesulfame K | 175.00 mg |
| Sodium saccharine | 40.00 mg |
| Neohesperidine DC | 2.50 mg |
| Flavouring | 300.00 mg |
| Inulin | 1000.00 mg |
| Mannitol | 2412.50 mg |

The invention claimed is:

1. A pharmaceutical composition comprising:
   Tribulus terrestris, Turnera diffusa and Cinnamon cassia extracts in the weight ratio of 1.5–3.5:1–2:0.1–0.4 respectively;
   extract of Ginkgo biloba, and optionally
   arginine or a physiologically equivalent ester, or salt thereof
in admixture with a suitable carrier or excipient.

2. The composition as claimed in claim 1, wherein the weight ratio of the Tribulus terrestris, Turnera diffusa and Cinnamon cassia extracts is 2.5:1.5:0.2.

3. The composition as claimed in claim 2, wherein the Ginkgo biloba extract is constituted by a fraction of apigenin dimeric flavonoids.

4. The composition as claimed in claim 1, wherein the Ginkgo biloba extract is constituted by a fraction of apigenin dimeric flavonoids.

5. The composition as claimed in claim 4, containing comprising Tribulus terrestris, Turnera diffusa and Cinnamon cassia extracts and L-arginine or L-arginine hydrochloride in the weight ratio of 1.5–3.5:1–2:0.1–0.4:0.5–1.5 respectively.

6. The composition as claimed in claim 4, containing 50 mg of a fraction of apigenin dimeric flavonoids.

7. The composition as claimed in claim 6, containing comprising Tribulus terrestris, Turnera diffusa and Cinnamon cassia extracts and L-arginine or L-arginine hydrochloride in the weight ratio of 1.5–3.5:1–2:0.1–0.4:0.5–1.5 respectively.

8. The composition as claimed in claim 1, containing comprising Tribulus terrestris, Turnera diffusa and Cinnamon cassia extracts and L-arginine or L-arginine hydrochloride in the weight ratio of 1.5–3.5:1–2:0.1–0.4:0.5–1.5 respectively.

9. The composition as claimed in claim 8, wherein the weight ratio of the Tribulus terrestris, Turnera diffusa and Cinnamon cassia extracts and L-arginine or L-arginine hydrochloride is 2.5:1.5:0.2:1.

10. A method for treating impotence, erectile dysfunction, reduced libido, frigidity and anorgasmia in a subject, comprising administering to said subject in need thereof an effective amount of a composition according to claim 1.

11. A method for treating sexual dysfunction in a male or female, comprising administering to said male or female an effective amount of a composition comprising Tribulus terrestris, Turnera diffusa and Cinnamon cassia extracts with a weight ratio of 1.5–3.5:1–2:0.1–0.4 respectively in combination with Ginkgo biloba extract, and optionally arginine or a physiologically equivalent ester, or thereof.

* * * * *